United States Patent [19]

Nagarajan et al.

[11] Patent Number: 4,552,701
[45] Date of Patent: Nov. 12, 1985

[54] GLYCOPEPTIDE ANTIBIOTICS AND PROCESS OF PREPARATION

[75] Inventors: Ramakrishnan Nagarajan; Amelia A. Schabel, both of Indianapolis, Ind.

[73] Assignee: Eli Lilly and Company, Indianapolis, Ind.

[21] Appl. No.: 600,727

[22] Filed: Apr. 16, 1984

[51] Int. Cl.$^4$ .................... C07C 103/52; C07H 15/20
[52] U.S. Cl. ............................ 260/112.5 R; 536/7.1; 536/16.8; 536/18.1
[58] Field of Search ...................... 536/7.1, 16.8, 18.1; 424/181, 180; 260/112.5 R; 514/8, 9, 25

[56] References Cited

U.S. PATENT DOCUMENTS

| | | | |
|---|---|---|---|
| 3,067,099 | 12/1962 | McCormick et al. | 167/65 |
| 4,196,280 | 4/1980 | Umezawa et al. | 536/7.1 |
| 4,299,953 | 11/1981 | Hamill et al. | 536/7.1 |

OTHER PUBLICATIONS

Donald J. McGraw, "The Antibiotic Discovery Era (1940–1960): Vancomycin as an Example of the Era," Thesis at Oregon State University, 1975, pp. 78–142.
F. J. Marshall, "Structure Studies on Vancomycin," *J. Med. Chem.* 8, 18–22, (1965).
G. M. Sheldrick et al., "Structure of Vancomycin and its Complex with Acetyl–D–alanyl–D–alanine," *Nature* 271, 223–225, (1978).
C. M. Harris et al., "Structure of the Glucopeptide Antibiotic Vancomycin, Evidence for an Asparagine Residue in the Peptide," *J. Am. Chem. Soc.*, 104, pp. 4293–4295.
"Vancomycin and Factor A," Report by Eli Lilly and Company sent to the U.S. Food and Drug Administration on Mar. 5, 1963.
G. K. Best et al., "Chromatographic Separation of the Vancomycin Complex," *Antimicrob. Agents & Chemotherapy*–1968, 115–119.
R. R. Pfeiffer, "Structural Features of Vancomycin," in *Reviews of Infectious Diseases,* vol. 3 Supplement (1981).

*Primary Examiner*—Johnnie R. Brown
*Attorney, Agent, or Firm*—Nancy J. Harrison; Arthur R. Whale

[57] ABSTRACT

Desvancosaminyl- and des(vancosaminyl-O-glucosyl) glycopeptides, and methods for their preparation by treating a glycopeptide selected from vancomycin, A51568A, A51568B, M43A and M43D with trifluoroacetic acid under controlled conditions, are provided. The new glycopeptides are useful antibacterial agents.

14 Claims, No Drawings

GLYCOPEPTIDE ANTIBIOTICS AND PROCESS OF PREPARATION

SUMMARY OF THE INVENTION

This invention relates to novel glycopeptide derivatives of formula 1:

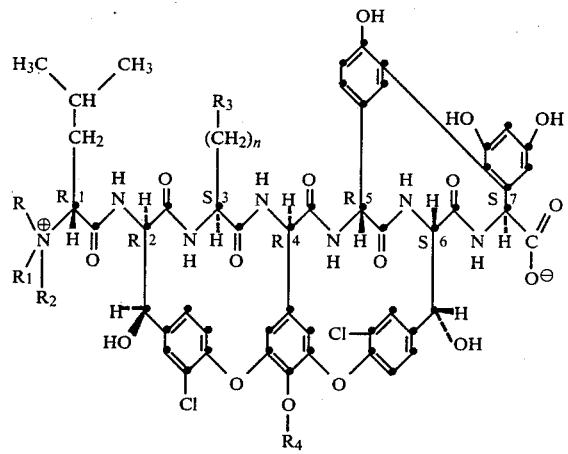

wherein
R, $R_1$ and $R_2$ are hydrogen or methyl;
$R_3$ is $CONH_2$;
$R_4$ is hydrogen or $\beta$-O-glucosyl; and
n is 1 or 2;
provided that, (1) when n is 2, R, $R_1$ and $R_2$ must be hydrogen, and (2) when R, $R_1$ and $R_2$ are methyl, $R_4$ must be hydrogen; and to the salts of these compounds.

Also included in this invention are methods of preparing the formula 1 compounds by treating a glycopeptide antibiotic selected from vancomycin, A51568 factor A (A51568A), A51568 factor B (A51568B), M43A and M43D with trifluoroacetic acid (TFA) under controlled temperature conditions to remove the α-O-vancosaminyl or α-O-Vancosaminyl-β-O-glucosyl groups from these antibiotics. For convenience, the terms 'vancosaminyl' and 'vancosaminyl-o-glucosy' will be used herein to denote the α-O-vancosaminyl and α-O-vancosaminyl-β-O-glucosyl units.

The formula 1 compounds retain excellent antibacterial activity, especially against gram-positive microorganisms. Thus, useful compositions containing the 1 compounds and methods of treating infections using the 1 compounds are also aspects of this invention.

DETAILED DESCRIPTION

This invention relates to new glycopeptide derivatives having formula 1 and to methods for preparing these derivatives. The formula 1 compound have useful antibacterial activity.

New, improved antibiotics are continually in demand, particularly for the treatment of human diseases. Increased potency, expanded spectrum of bacterial inhibition, increased in vivo efficacy, and improved pharmaceutical properties (such as greater oral absorption, higher blood or tissue concentrations, longer in vivo half life, and more advantageous rate or route of excretion and rate or pattern of metabolism) are some of the goals for improved antibiotics.

In the search for new antibiotics, structural modification of known antibiotics is attempted whenever possible. However, many antibiotics, including the glycopeptides, have such complex structures that even small changes are difficult to make. Processes for modifying known antibiotics to make new active derivatives continue, therefore, to be of grat importance.

The formula 1 compounds are members of the glycopeptide group of antibiotics. The compounds are prepared from the glycopeptides vancomycin (see, for example, U.S. Pat. No. 3,067,099), antibiotic A51568 factors A and B (see the copending applications of M. M. Hoehn and G. G. Marconi, Ser. No. 562,255 filed Dec. 16, 1983, now U.S. Pat. No. 4,495,179, and LaVerne D. Boeck et al., Ser. No. 561,008, filed Dec. 13, 1983); antibiotic M43A, which is the subject of a copending application of Harvey M. Higgins, Mack H. McCormick and Kurt E. Merkel entitled ANTIBIOTIC M43A, Ser. No. 600,729, and antibiotic M43D, which is the subject of a copending application of Kurt E. Merkel entitled ANTIBIOTIC M43D, Ser. No. 600,725, both of which are filed herewith this even date.

Two other closely related compounds, M43B and M43C, are the subject of a copending application of Karl H. Michel entitled ANTIBIOTICS M43B and M43C, Ser. No. 600,726, also filed herewith this even date. The structural relationships of these glycopeptide antibiotics are provided in formulas 2–8 which follow (compounds 9–13 are specific formula 1 compounds):

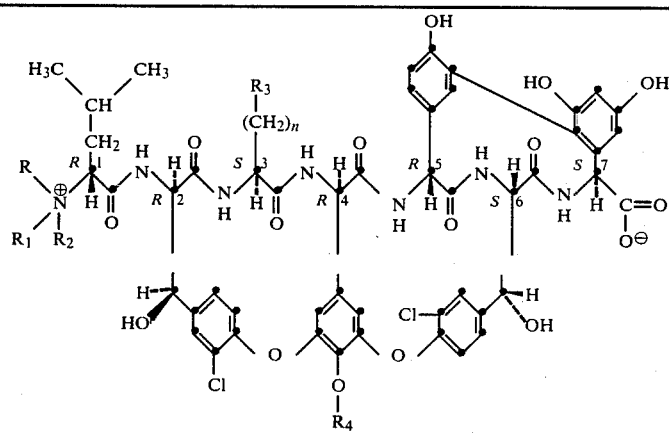

Compound

-continued

| No. | Compound | R | $R_1$ | $R_2$ | $R_3$ | n | $R_4$ |
|---|---|---|---|---|---|---|---|
| 2 | Vancomycin | H | H | $CH_3$ | $CONH_2$ | 1 | vancosaminyl-O—glucosyl |
| 3 | M43A | $CH_3$ | $CH_3$ | $CH_3$ | $CONH_2$ | 1 | " |
| 4 | M43B | $CH_3$ | $CH_3$ | $CH_3$ | COOH | 1 | " |
| 5 | M43C | $CH_3$ | $CH_3$ | $CH_3$ | $CONH_2$ | 1 | glucosyl |
| 6 | M43D | H | $CH_3$ | $CH_3$ | $CONH_2$ | 1 | vancosaminyl-O—glucosyl |
| 7 | A51568A | H | H | H | $CONH_2$ | 1 | vancosaminyl-O—glucosyl |
| 8 | A51568B | H | H | H | $CONH_2$ | 2 | " |
| 9 | Agluco-A51568A | H | H | H | $CONH_2$ | 1 | H |
| 10 | Algucovancomycin | H | H | $CH_3$ | $CONH_2$ | 1 | H |
| 11 | Agluco-M43A | $CH_3$ | $CH_3$ | $CH_3$ | $CONH_2$ | 1 | H |
| 12 | Desvancosamine-A51568A | H | H | H | $CONH_2$ | 1 | glucosyl |
| 13 | Desvancosamine-Vancomycin | H | H | $CH_3$ | $CONH_2$ | 1 | glucosyl |

The formula 1 compounds are prepared by controlled treatment of an antibiotic selected from vancomycin, A51568A, A51568B, M43A and M43D with trifluoroacetic acid (TFA).

The new derivatives are close to vancomycin in structure and also in activity. They are, therefore, valuable additions to this group of antibiotics.

The formula 1 compounds are shown as zwitterions. Those in the art will recognize, however, that each has a carboxyl group, one or two amino groups and three phenolic groups which can react to form various salts. All such forms of the formula 1 compounds are part of this invention. The salts are useful, for example, for separating and purifying the antibiotics. In addition, the salts have an improved solubility in water.

The formula 1 salts are prepared using standard procedures for salt preparation. For example, the zwitterion can be neutralized with an appropriate acid to form an acid addition salt.

The formula 1 acid addition salts are particularly useful. Representative suitable salts include those salts formed by standard reactions with both organic and inorganic acids such as, for example, sulfuric, hydrochloric, phosphoric, acetic, succinic, citric, lactic, maleic, fumaric, cholic, pamoic, mucic, D-glutamic, d-camphoric, glutaric, glycolic, phthalic, tartaric, formic, lauric, stearic, salicylic, methanesulfonic, benzenesulfonic, sorbic, picric, benzoic, cinnamic and like acids.

Pharmaceutically acceptable acid addition salts are an especially preferred group of salts of this invention.

The formula 1 compound wherein R, $R_1$ and $R_4$ are hydrogen, $R_2$ is methyl, $R_3$ is $CONH_2$ and n is 1 is called aglucovancomycin (Compound No. 10). Previously, a compound thought to be aglucovancomycin was reported by Marshall [J. Med. Chem. 8, 18–22 (1965)]. This compound was prepared by treating vancomycin with hot hydrochloric acid. The product of this reaction, however, when examined by high performance liquid chromatography (HPLC), was found to be a mixture. We have been able to obtain aglucovancomycin in substantially pure form by separating this mixture, using preparative HPLC. Purified aglucovancomycin has good in vitro antibacterial activity.

The other component in Marshall's "aglucovancomycin" was found to be a degradation product. This component is isomeric with degradation product CDP-I previously described by Marshall.

We have also discovered a method for selectively removing the vancosaminyl, or vancosaminyl-O-glucosyl moieties from vancomycin, A51568A, A51568B, M43A and M43D by treating these compounds with TFA while controlling the temperature of the reaction. At low temperatures, i.e., from about $-10°$ to about $-20°$ C., the vancosaminyl sugar is selectively removed. Only a very minor amount of the corresponding aglucone is formed at these temperatures. At higher temperatures, i.e. from about 20° to about 70° C., the corresponding aglucones are the major products, and the corresponding desvancosaminyl compounds are minor products.

An important advantage of this process, therefore, is that, by selecting the appropriate temperature for the reaction, the desired compound is the major product of the reaction. Another advantage of the method is that undesired degradation products such as CDP-I and CDP-II are not formed in appreciable amounts.

In one aspect, therefore, this invention provides methods for producing aglucovancomycin, agluco-A51568A, agluco-A51568B, agluco-M43A or agluco-M43D by treating vancomycin, A51568A, A51568B, M43A or M43D, respectively, with TFA at temperatures from about 20° to about 70° for from about one to about eight hours until the desired compound is formed. Although this process can be carried out at room temperature for from 6 to 8 hours, it may also be carried out at higher temperatures, e.g. 50° C., for shorter periods of time, e.g. 1–2 hours. Higher temperatures are preferable when minimizing formation of the corresponding desvancosamine derivatives is desired.

Another aspect of this invention relates to a process for preparing M43C or a compound of formula 1 wherein $R_4$ is glucosyl by treating a compound selected from M43A, vancomycin, A51568A, A51568B or M43D with TFA at a temperature of from about $-10°$ C. to about $-20°$ C. for a period of about 12–66 hours until the desired product is attained. A preferred temperature for this method is about $-15°$ C., and a preferred time is about 16 hours. This method for preparing M43C is more efficient than that of Michel, supra. Using the earlier method, only minor amounts of the compound could be obtained.

The formula 1 compounds wherein $R_4$ is glucosyl and antibiotic M43C are useful intermediates for preparing formula 1 compounds wherein $R_4$ is hydrogen. This is accomplished by treating M43C or a formula 1 compound wherein $R_4$ is glucosyl with TFA at about 50° C. for a period of from about 1 to 2 hours. This invention also relates, therefore, to a process for preparing a compound of formula 1 wherein $R_4$ is hydrogen by treating a compound selected from M43C or a formula 1 compound wherein $R_4$ is glucosyl with TFA at a temperature from about 20° to about 70° C. for from about one to about six hours until the desired product is formed. A preferred temperature range for this process is from about 55° to about 65° C., and a preferred time is from one to three hours.

The formula 1 compounds inhibit the growth of a broad spectrum of pathogenic bacteria, especially gram-positive bacteria. Table I summarizes the minimal inhibitory concentrations (MIC's) at which the compounds inhibit certain organisms, as determined by standard agar-dilution assays.

TABLE 1

In Vitro Activity of Formula 1 Compounds

| Organism | MIC (mcg/ml) Compound No. | | | | | |
|---|---|---|---|---|---|---|
| | 5 | 9 | 10 | 11 | 12 | 13 |
| Staphylococcus aureus NRRL B313 | 2 | 0.5 | 0.5 | 2 | 2 | 8 |
| Staphylococcus aureus V41 | 2 | 0.5 | 1 | 2 | 2 | 8 |
| Staphylococcus aureus X400 | 2 | 0.5 | 1 | 2 | 2 | 8 |
| Staphylococcus aureus S13E | 2 | 0.5 | 1 | 2 | 2 | 8 |
| Staphylococcus epidermidis EP11 | 8 | 1 | 2 | 2 | 4 | 16 |
| Staphylococcus epidermidis 222 | 4 | 1 | 1 | 2 | 4 | 8 |
| Streptococcus pyogenes C203 | 1 | 1 | 0.5 | 2 | 2 | 4 |
| Streptococcus pneumoniae Park 1 | 1 | 0.5 | 0.5 | 1 | 1 | 4 |
| Streptococcus faecium ATCC 9790 | 4 | 1 | 1 | 2 | 4 | 8 |
| Streptococcus sp. group D 2041 | 8 | 2 | 64 | 4 | 8 | 32 |
| Haemophilus influenzae C.L. | >64 | 128 | 64 | 128 | >128 | >128 |
| Haemophilus influenzae 76 | 64 | 128 | 64 | 32 | >128 | 128 |
| Escherichia coli N10 | >64 | >128 | >128 | >128 | >128 | >128 |
| Escherichia coli EC14 | >64 | >128 | >128 | >128 | >128 | >128 |
| Escherichia coli TEM | >64 | >128 | 64 | >128 | 128 | >128 |
| Klebsiella pneumonia X26 | >64 | >128 | >128 | >128 | >128 | >128 |
| Klebsiella pneumonia X68 | >64 | >128 | >128 | >128 | >128 | >128 |
| Klebsiella pneumonia KAE | >64 | >128 | >128 | >128 | >128 | >128 |

The formula 1 compounds also inhibit the growth of anaerobic bacteria. Table II summarizes the susceptibility of various anaerobic isolates to two formula 1 compounds.

TABLE II

Susceptibility of Anaerobic Bacterial Isolates to Formula 1 Compounds

| ANAEROBIC BACTERIA | MIC ($\mu$g/ml)[a] Compound No. | |
|---|---|---|
| | 9 | 10 |
| Clostridium difficile 2994 | 1 | 8 |
| Clostridium perfringens 81 | 1 | 8 |
| Clostridium septicum 1128 | 1 | 8 |
| Eubacterium aerofaciens 1235 | 1 | 128 |
| Peptococcus asaccharolyticus 1302 | 1 | 64 |
| Peptococcus prevoti 1281 | 1 | 8 |
| Peptostreptococcus anaerobius 1428 | ≧0.5 | 32 |
| Peptostreptococcus intermedius 1264 | 1 | >128 |
| Propionibacterium acnes 79 | 1 | 8 |
| Bacteroides fragilis 111 | 64 | >128 |
| Bacteroides fragilis 1877 | 64 | 128 |
| Bacteroides fragilis 1936B | 64 | >128 |
| Bacteroides thetaiotaomicron 1438 | 64 | >128 |
| Bacteroides melaninogenicus 1856/28 | >128 | >128 |
| Bacteroides melaninogenicus 2736 | 4 | 128 |
| Bacteroides vulgatis 1211 | 1 | 128 |
| Bacteroides corrodens 1874 | 64 | >128 |
| Fusobacterium symbiosum 1470 | 4 | 8 |
| Fusobacterium necrophorum 6054A | ≧0.5 | 2 |

[a]MIC's were determined by the agar-dilution method; endpoints were read after 24-hrs. incubation.

The formula 1 compounds have also shown in vivo antimicrobial activity against experimental bacterial infections. When two doses of test compound were administered to mice in experimental infections, the activity observed was measured as an $ED_{50}$ value [effective dose in mg/kg to protect 50% of the test animals: see Warren Wick, et al., *J. Bacteriol.* 81, 233-235 (1961)]. $ED_{50}$ values observed are given in Table III.

TABLE III $ED_{50}$ Values for Formula 1 Compounds

| Organism | Route of Administration | $ED_{50}$ (mg/kg/2) Compound No. | | |
|---|---|---|---|---|
| | | 9 | 10 | 11 |
| Staphylococcus aureus | subcutaneous | 0.74 | 8.75 | 3.06 |
| Streptococcus pyogenes | " | 2.0 | 22.3 | 3.63 |
| Streptococcus pneumoniae | " | 1.8 | 16.54 | 3.06 |

Pharmaceutical formulations of formula 1 compounds and their salts are also part of this invention. Thus, a formula 1 compound, preferably as a pharmaceutically acceptable salt, can be formulated for oral or parenteral administration for the therapeutic or prophylactic treatment of bacterial infections. For example, the compound can be admixed with conventional pharmaceutical carriers and excipients and used in the form of tablets, capsules, elixirs, suspensions, syrups, wafers and the like. The compositions comprising a formula 1 compound will contain from about 0.1 to about 90% by weight of the active compound, and more generally from about 10 to about 30%. The compositions may contain common carriers and excipients, such as corn starch or gelatin, lactose, sucrose, microcrystalline cellulose, kaolin, mannitol, dicalcium phosphate, sodium chloride and alginic acid. Disintegrators commonly used in the formulations of this invention include croscarmellose sodium, microcrystalline cellulose, corn starch, sodium starch glycolate and alginic acid. Tablet binders that can be included are acacia, methylcellulose, sodium carboxymethylcellulose, polyvinylpyrrolidone (Povidone), hydroxypropyl methylcellulose, sucrose, starch and ethylcellulose. Lubricants that can be used include magnesium stearate or other metallic stearates, stearic acid, silicone fluid, talc, waxes, oils and colloidal silica. Flavoring agents such as peppermint, oil of wintergreen, cherry flavoring or the like can also be used. It may be desirable to add a coloring agent to make the dosage form more esthetic in appearance or to help indentify the product.

For intravenous (IV) use, a water soluble form of the antibiotic can be dissolved in one of the commonly used intravenous fluids and administered by infusion. Such fluids as, for example, physiological saline, Ringer's solution or 5% dextrose solution can be used.

For intramuscular preparations, a sterile formulation of a suitable soluble salt form of the compound, for example the hydrochloride salt, can be dissolved and administered in a pharmaceutical diluent such as Water-for-Injection, physiological saline or 5% glucose solution. A suitable insoluble form of the compound may be prepared and administered as a suspension in an aqueous base or a pharmaceutically acceptable oil base, e.g. an ester of a long chain fatty acid such as ethyl oleate.

For oral use, a sterile formulation of suitable salt form of the antibiotic, for example, the hydrochloride salt, formulated in a diluent such as distilled or deionized water, is particularly useful.

Alternatively, the unit dosage form of the antibiotic can be a solution of the antibiotic or preferably a salt thereof in a suitable diluent in sterile, hermetically sealed ampoules. The concentration of the antibiotic in the unit dosage may vary, e.g. from about 1 percent to about 50 percent depending on the particular form of the antibiotic and its solubility and the dose desired by the physician.

In a further aspect, this invention provides a method for treating or controlling infectious diseases, especially those caused by gram-positive microorgnisms, in animals. This method comprises administering to the animal a dose between about 0.5 and about 100 mg/kg of a formula 1 compound or its pharmaceutically acceptable salt. A preferred dose is from about 10 to about 60 mg/kg of active compound. A typical daily dose for an adult human is from about 250 mg to about 1.0 g.

In practicing this method, the antibiotic can be administered in a single daily dose or in multiple doses per day. The treatment regime may require administration over extended periods of time, e.g., for several days or for from two to three weeks. The amount per administered dose or the total amount administered will depend on such factors as the nature and severity of the infection, the age and general health of the patient, the tolerance of the patient to the antibiotic and the microorganism or microorganisms involved in the infection.

A convenient method of practicing the treatment method is to administer the antibiotic via IV infusion. In this procedure a sterile formulation of a suitable soluble salt of the antibiotic is incorporated in a physiological fluid, such as 5% dextrose solution, and the resulting solution is infused slowly IV. Alternatively, the piggyback method of IV infusion can also be used.

In another embodiment, this invention relates to methods of increasing feed-utilization efficiency in poultry, swine, sheep and cattle, of promoting growth rates in cattle raised for meat production and of enhancing milk production in lactating ruminants. For increasing feed utilization efficiency and promoting growth, a formula 1 compound is administered orally in a suitable feed in an amount of from about 2 to about 200 grams per ton of total feed. For beef cattle, for example, a range of about 12 to 3000 mg/head/day is suitable. For enhancing milk production in lactating ruminants, oral administration of a daily amount of from about 0.04 to about 16 mg/kg of body weight (or about 25 to about 5000 mg/ruminant/day) is suggested.

The following examples are provided to illustrate this invention.

EXAMPLE 1

Preparation of Agluco-A51568A (9) and Desvancosamine-A51568A (12)

A51568A (4.5 g) was dissolved in 50 ml of trifluoroacetic acid (TFA). The reaction mixture was stirred at room temperature for 5 hours and then was evaporated to dryness under vacuum. A small amount of water was added to the residue, and the solution was freeze-dried. The crude product was purified by reversed-phase high performance liquid chromatography (HPLC), using the system described in Example 6 to give 435 mg of agluco-A51568A and 1.463 g of desvancosamine-A51568A. The products were identified by nuclear magnetic resonance spectrometry (NMR) and fast-atom-bombardment mass spectrometry (FABMS).

EXAMPLE 2

Preparation of Aglucovancomycin (10) and Desvancosamine-vancomycin (13)

Vancomycin free base (9.2 g) was dissolved in TFA (100 ml). The reaction mixture was stirred in a 50° C. oil bath for 3½ hours and then was cooled to room temperature. Excess TFA was evaporated under vacuum. The residue was treated with a small amount of water and freeze-dried. The grayish product was purified by reversed-phase HPLC, using conditions described in Example 6, to give aglucovancomycin in 30% yield and 450 mg of desvancosamine-vanocomycin. The products were identified by NMR and FABMS.

EXAMPLE 3

Preparation of Desvancosamine-Vancomycin (13)

Vancomycin was dissolved in TFA and stirred for three days at $-15°$ C. This procedure gave a crude product which was a 1:1 mixture of starting material and desvancosamine-vancomycin. Purification by reversed-phase HPLC (see Example 6) gave desvancosamine-vancmycin. In addition, aglucovancomycin was a minor prodct of the reaction.

EXAMPLE 4

Preparation of Agluco-M43A (11)

M43A (642.7 mg) was dissolved in TFA (15 ml), and the solution was stirred in a 55°-60° C. oil bath for 3 hours. The reaction mixture was cooled to room temperature, and excess TFA was removed under vacuum. A little water was added, and the product was freeze-dried. The freeze-dried material was purified by reversed-phase HPLC, using the conditions of Example 6, to give 180.9 mg of agluco-M43A, as identified by NMR and FABMS.

EXAMPLE 5

Preparation of M43C (5) (Desvancosamine-M43A)

M43A (398 mg) was dissolved in TFA (10 ml). The resulting solution was kept at $-15°$ C. for 30 hours, and then was evaporated to dryness and freeze-dried. The reaction product was purified by reversed-phase HPLC, using the system described in Example 6, to give 40 mg of M43C as identified by NMR and FABMS.

EXAMPLE 6

Separation of Formula 1 Compounds by Analytical HPLC

The formula 1 compounds can be examined by analytical HPLC, using the following system (starting materials are included for comparison):

| Column: | Beckman Ultrasphere (5μ particle size), ODS, 25 cm |
|---|---|
| Mobile Phase: | Solvent A: CH₃CN/TEAP (5:95) |
| | Solvent B: CH₃CN/TEAP (2:3) |
| | [TEAP = 0.5% aqueous triethylamine adjusted to pH 3 with conc. phosphoric acid] |
| Gradient: | 9% B to 70% B over a 40-min. period; then hold for 5 min. at 70% B |
| Flow Rate: | 1.0 ml/min. |
| Detection: | UV at 254 nm |

| Compound | Retention Time (min.) |
|---|---|
| A51568 factor A | 8.96 |
| vancomycin | 12.23 |
| desvancosamine-A51568A | 17.59 |
| desvancosamine-vancomycin | 20.38 |
| M43A | 24.26 |
| M43C | 29.58 |
| agluco-A51568A | 36.97 |
| aglucovancomycin | 37.72 |
| agluco-M43A | 39.79 |

We claim:

1. A compound of the formula:

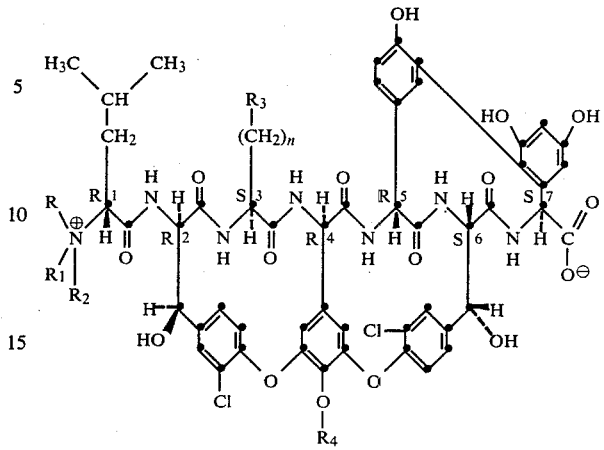

wherein
R, R₁ and R₂ are hydrogen or methyl;
R₃ is CONH₂;
R₄ is hydrogen or β-O-glucosyl; and
n is 1 or 2;
provided that, (1) when n is 2, R, R₁ and R₂ must be hydrogen, and (2) when R, R₁ and R₂ are methyl, R₄ must be hydrogen; and its salts.

2. A compound of claim 1 wherein R₄ is hydrogen and n is 1.

3. The compound of claim 2 wherein R, R₁ and R₂ are hydrogen.

4. The compound of claim 2 wherein R and R₁ are hydrogen and R₂ is methyl.

5. The compound of claim 2 wherein R, R₁ and R₂ are methyl.

6. A compound of claim 1 wherein R₄ is β-O-glucosyl and n is 1.

7. The compound of claim 6 wherein R, R₁ and R₂ are hydrogen.

8. The compound of claim 6 wherein R and R₁ are hydrogen and R₂ is methyl.

9. A process for preparing M43C or a compound of claim 1 wherein R₄ is β-O-glucosyl which comprises treating a compound selected from vancomycin, A515-68A, A51568B, M43A or M43D with trifluoroacetic acid at a temperature of from about −10° to about −20° C. for a period of from about 12 to about 66 hours until the compound is formed.

10. A process of claim 9 wherein the temperature is about −15° C. and the period is about 16 hours.

11. A process for preparing a compound of claim 1 wherein R₄ is hydrogen which comprises treating a compound selected from vancomycin, A51568A, A51568B, M43A or M43D with trifluoroacetic acid at a temperature of from about 20° to about 70° C. for a period of from about one to about eight hours until the compound is formed.

12. A process of claim 11 wherein the temperature is about 50° C. and the period is from one to two hours.

13. A process for preparing a compound of claim 1 wherein R₄ is hydrogen which comprises treating M43C, desvancosamine-vancomycin, desvancosamine-A51568A desvancosamine-A51568B or desvancosamine-M43D with trifluoroacetic acid at a temperature of from about 20° to about 70° C. for a period of from one to six hours until the compound is formed.

14. A process of claim 13 wherein the temperature is from about 55° to 65° C. and the period is about one to three hours.

* * * * *